(12) United States Patent
Nagase et al.

(10) Patent No.: US 7,700,741 B2
(45) Date of Patent: Apr. 20, 2010

(54) HIGH AFFINITY ANTI-$N^1,N^{12}$-DIACETYLSPERMINE MONOCLONAL ANTIBODY

(75) Inventors: Yusei Nagase, Hyogo (JP); Shingo Shinagawa, Hyogo (JP); Masao Kawakita, Tokyo (JP); Kyoko Hiramatsu, Tokyo (JP); Mika Ito, Kumamoto (JP); Yosuke Mizukami, Kumamoto (JP); Chiemi Minoda, Kumamoto (JP)

(73) Assignee: Trans Genic Inc., Kumamoto (JP)

( * ) Notice: Subject to any disclaimer, the term of this patent is extended or adjusted under 35 U.S.C. 154(b) by 798 days.

(21) Appl. No.: 11/263,355

(22) Filed: Oct. 31, 2005

(65) Prior Publication Data

US 2006/0166297 A1  Jul. 27, 2006

(30) Foreign Application Priority Data

Jan. 24, 2005 (JP) ............................. 2005-014913

(51) Int. Cl.
*C12N 15/02* (2006.01)
(52) U.S. Cl. ..................... 530/388.1; 435/7.92; 435/335
(58) Field of Classification Search ........................ None
See application file for complete search history.

(56) References Cited

FOREIGN PATENT DOCUMENTS

JP            H11-75839          3/1999

OTHER PUBLICATIONS

Hamaoki et al., J. Biochem. 2002, vol. 132, p. 783-788.*
Masayuki Sugimoto et al., Significance of Urinary $N^1,N^8$-Diacetylspermidine and $N^1,N^{12}$-Diacetylspermine as Indicators of Neoplastic Disease, *J Cancer Res Clin Oncol*, 1995, 121:317-319, Springer-Verlag.
Kyoko Hiramatsu et al., Diagnostic and Prognostic Usefulness of $N^1,N^8$-Diacetylspermidine and $N^1,N^{12}$-Diacetylspermine in Urine as Novel Markers of Malignancy, *J Cancer Res Clin Oncol*, 1997, 123:539-545, Springer-Verlag.
Kyoko Hiramatsu et al., Determination of Amounts of Polyamines Excreted in Urine: Demonstration of $N^1,N^8$-Diacetylspermidine and $N^1,N^{12}$-Diacetylspermine as Components Commonly Occurring in Normal Human Urine, *J. Biochem*, 1995, vol. 117, No. 1, pp. 107-112.
Kyoko Hiramatsu et al., Development of a Sensitive and Accurate Enzyme-Linked Immunosorbent Assay (ELISA) System That Can Replace HPLC Analysis for the Determination of $N^1$, $N^{12}$-Diacetylspermine in Human Urine, *J. Biochem*, 1998, vol. 124, No. 1, pp. 231-236.
S. Kubota, Nippon Rinsho, vol. 53 (supplemental), pp. 501-505 (Feb. 28, 1995) (w/ English translation).

* cited by examiner

*Primary Examiner*—Michael Szperka
*Assistant Examiner*—Yunsoo Kim
(74) *Attorney, Agent, or Firm*—Dickstein Shapiro LLP

(57) ABSTRACT

The present invention provides an anti-diacetylspermine specific monoclonal antibody which satisfies a specific measuring condition in an immunoreaction system between a solid-phased diacetylspermine and the anti-diacetylspermine specific monoclonal antibody, wherein the immunoreaction system comprises a sample diacetylspermine or sample $N^1$-acetylspermidine to inhibit the immunoreaction; and the specific measuring condition is that the 50% inhibition activity against the immunoreaction by the diacetylspermine in the sample is at least 1,000 times as much as the 50% inhibition activity against the immunoreaction by the $N^1$-acetylspermidine in the sample.

3 Claims, 7 Drawing Sheets

HIGH AFFINITY ANTI-N$^1$,N$^{12}$-DIACETYLSPERMINE MONOCLONAL ANTIBODY

FIELD OF THE INVENTION

The present invention relates to a monoclonal antibody to diacetylspermine.

BACKGROUND OF THE INVENTION

Polyamine is a general term for those alkylamines with two or more amino groups. There are four types of polyamines [putrescine ($H_2N(CH_2)_4NH_2$), cadaverine ($H_2N(CH_2)_5NH_2$), spermidine ($H_2N(CH_2)_4NH(CH_2)_3NH_2$) and spermine ($H_2N(CH_2)_3NH(CH_2)_4NH(CH_2)_3NH_2$)] and acetylated forms thereof in the human body.

Relatively recently, it was found that two types of diacetylpolyamines [N$^1$,N$^8$-diacetylspermidine (hereinafter expressed as "DiAcSpd") and N$^1$,N$^{12}$-diacetylspermine (hereinafter expressed as "DiAcSpm")] are excreted in urine though very small in quantities. While these components occupy only 1.4% and 0.6% of the total polyamine, respectively, in the urine of healthy persons, the ratios of these components remarkably increase in the urine of cancer patients as compared to other polyamine components. Further, it has been shown that these components also have other characteristics of tumor markers (Sugimoto, M. et al., J. Cancer Res. Clin. Oncol., 121, 317-319 (1995); Hiramatsu, K. et al., J. Cancer Res. Clin. Oncol., 123, 539-545 (1997)).

Initially, DiAcSpd and DiAcSpm were quantitatively determined by a method which is a combination of a fractionation measuring system by HPLC and a detection system using enzyme (Hiramatsu, K. et al., J. Biochem., 117, 107-112 (1995)). However, more simple measuring methods have been developed. In particular, with respect to the measurement of DiAcSpm, an ELISA method using a specific antibody was developed recently (Hiramatsu, K. et al., J. Biochem., 124, 231-236 (1998)).

Recently, Fujiwara et al. prepared monoclonal antibodies to DiAcSpm (Japanese Unexamined Patent Publication No. H11-75839). With these antibodies, 50% binding inhibition activity against immunoreaction with DiAcSpm is only about 100 times as much as 50% binding inhibition activity against immunoreaction with N$^1$-acetylspermidine (hereinafter expressed as "N$^1$-AcSpd") and is only about 20 times as much as 50% binding inhibition activity against immunoreaction with N$^1$-acetylspermine (hereinafter expressed as "N$^1$-AcSpm") which is a monoacetylated form of spermine. Since the amount of N$^1$-AcSpd in the urine of healthy persons is about 25 times as much as the amount of DiAcSpm therein, the crossreactivity of the above antibody with N$^1$-AcSpd in the urine of healthy persons is 25 when the crossreactivity of the antibody with DiAcSpm therein is taken as 100. Therefore, the antibody may yield false-positive results. Accordingly, in order to enhance the measuring sensitivity for DiAcSpm, a DiAcSpm-specific monoclonal antibody whose crossreactivities with N$^1$-AcSpd and N$^8$-acetylspermidine (hereinafter expressed as "N$^8$-AcSpd") are still lower is required.

SUMMARY OF THE INVENTION

The present invention aims at providing a monoclonal antibody to DiAcSpm. The present invention also aims at providing a method of detecting DiAcSpm comprising reacting the above antibody with a biological sample; and a reagent for detection to be used in the method.

The present inventors have made intensive and extensive researches toward the solution of the above problem. As a result, they have found that by immunizing animals with antigen to raise antibody titers, leaving the animals until the antibody titers decrease, and then preparing antibody-producing cells, it possible to obtain a monoclonal antibody with which 50% binding inhibition activity against immunoreaction with DiAcSpm is at least 1,000 times as much as 50% binding inhibition activity against immunoreaction with N$^1$-acetylspermidine. Thus, the present invention has been achieved.

The present invention relates to the following.

(1) An anti-diacetylspermine specific monoclonal antibody which satisfies a specific measuring condition in an immunoreaction system between a solid-phased diacetylspermine and the anti-diacetylspermine specific monoclonal antibody, wherein the system comprises a sample diacetylspermine or sample N$^1$-acetylspermidine to inhibit the immunoreaction; and the specific measuring condition is that the 50% inhibition activity against the immunoreaction by the diacetylspermine in the sample is at least 1,000 times as much as the 50% inhibition activity against the immunoreaction by the N$^1$-acetylspermidine in the sample.

(2) The monoclonal antibody according to (1) above, wherein the concentration of the diacetylspermine in the sample is 1 nM or less.

(3) An anti-diacetylspermine specific monoclonal antibody which is produced by a cell strain having an accession number of FERM BP-10420.

(4) A cell strain which produces the monoclonal antibody according to (1) above.

(5) An anti-diacetylspermine specific monoclonal antibody-producing cell strain having an accession number of FERM BP-10420.

(6) A reagent for detecting diacetylspermine, comprising the monoclonal antibody according to any one of (1) to (3) above.

(7) A method of detecting DiAcSpm, comprising reacting the monoclonal antibody according to any one of (1) to (3) above with a biological sample.

Specific examples of the biological sample include urine and serum.

(8) A method of evaluating tumor, comprising using the results detected by the method according to (6) above as an indicator.

(9) A tumor diagnostic agent comprising the monoclonal antibody according to any one of (1) to (3) above.

(10) A method of preparing a monoclonal antibody, comprising the following steps:
  (a) leaving immunized animals at a stage when the antibody titers thereof have risen;
  (b) re-immunizing the animals when the antibody titers have decreased to 0.05-1 in the absorbance level;
  (c) collecting antibody-producing cells from the re-immunized animals;
  (d) preparing a fusion cell strain from the collected antibody-producing cells and myeloma cells; and
  (e) producing a monoclonal antibody using the resultant cell strain.

The monoclonal antibody of the invention reactive with DiAcSpm is capable of measuring DiAcSpm in samples such as urine with high sensitivity and specificity, and thus useful in diagnosis of cancer.

DETAILED DESCRIPTION OF THE INVENTION

Figure 1:
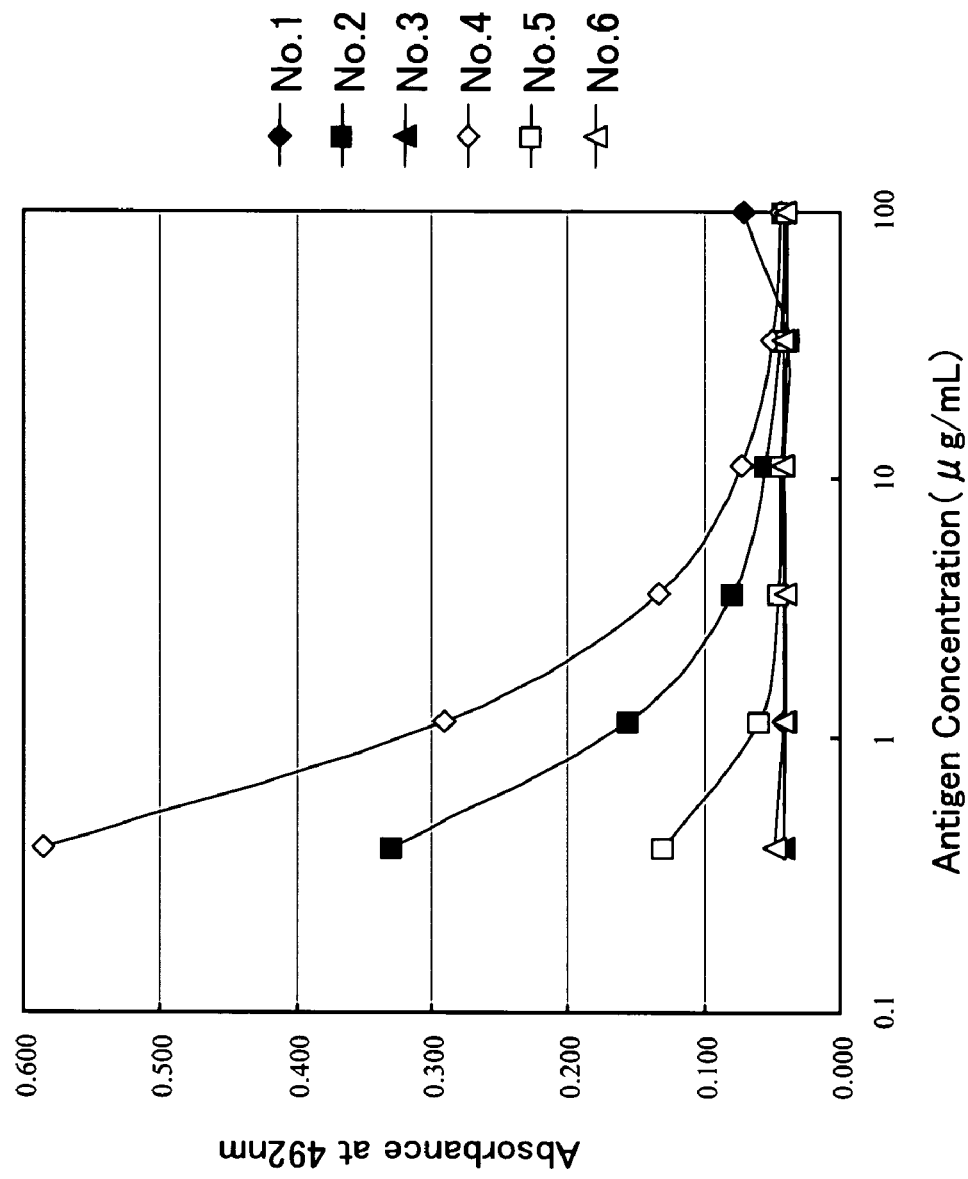
FIG. 1 is a diagram showing evaluation of immunizing antigens with absorbances at 492 nm.

Hereinbelow, the present invention will be described in detail.

All publications cited herein (e.g., prior art documents and patent publications, patents and other patent documents) are incorporated herein by reference in their entirety.

The antibody of the present invention has one, two or all of the following properties: (i) the concentration of DiAcSpm at which the immunoreaction of solid-phased DiAcSpm is inhibited 50% is 1 nM or less; (ii) crossreactivity with $N^1$-Ac-Spd (which is present in urine as a structure analog of DiAcSpm in an amount about 30-times greater than DiAcSpm) is 0.1% or less; or (iii) total crossreactivity with structure analogs of DiAcSpm present in urine is 5% or less.

1. An Outline of the Invention

DiAcSpm is a type of polyamine (which is a general term for low molecular weight alkylamines, specifically, alkylamines with two or more amino groups), and is an acetylated form of spermine ($H_2N(CH_2)_3NH(CH_2)_4NH(CH_2)_3NH_2$), one of the four polyamines present in the human body. Recently, it has been found that DiAcSpm is present at high concentrations in the urine of cancer patients.

However, a large quantity of structure analogs of DiAcSpm represented by AcSpd is present in biological samples, especially in urine samples. Therefore, interference by structure analogs must be taken into consideration. Briefly, in order to quantitatively determine DiAcSpm correctly by enzyme immunoassay, it is most important to obtain a monoclonal antibody showing high specificity to DiAcSpm. Such a monoclonal antibody is required for the establishment of a measuring kit. The present invention has been achieved to solve these problems.

The monoclonal antibody can be obtained by employing an animal immunization method that is different from conventional methods. Briefly, this immunization method is characterized by leaving once immunized animals for a while at a stage when antibody titers have risen to 2 or more in the absorbance level, further immunizing the animals when the antibody titers have decreased to 0.05-1, preferably 0.05-0.5, more preferably 0.05 in the absorbance level, and then preparing antibody-producing cells from the resultant animals.

The increased level of the antibody titer is 2 or more in the absorbance level.

The term "leaving" used herein means feeding animals without performing immunization. The period of leaving is 2-6 months, preferably 4-6 months, more preferably 6 months.

The decreased level of the antibody titer is 0.05-1, preferably 0.05-0.5, more preferably 0.05 in the absorbance level.

With respect to the method for obtaining the monoclonal antibody of the invention (hereinafter referred to as "anti-DiAcSpm antibody"), animals are immunized with an acetylspermine derivative of bovine serum albumin, and the resultant B cells are fused to myeloma cells to prepare hybridomas.

The anti-DiAcSpm antibody is the so-called hapten antibody. In the preparation of such hapten antibodies, the design of the molecular structure of a hapten-carrier conjugate has a large effect upon the performance of the resultant specific antibody. It is reported that antibodies prepared using spermine bound to BSA with glutaraldehyde as a hapten show higher reactivity with spermine or spermidine than reactivity with acetylpolyamines in competitive ELISA. Therefore, in order to prepare an antibody that reacts preferentially with acetylpolyamines, it is indispensable that acylamide bond is present in the hapten-carrier conjugate.

Here, it is also possible to use polyclonal antibodies to DiAcSpm as long as specificity to DiAcSpm is secured. However, polyclonal antibodies often include those antibodies which have high crossreactivities with other structure analogs such as acetylpolyamines. In such cases, antibodies highly specific to DiAcSpm must be prepared through several stages of purification process. In particular, because of the nature of hapten-carrier complexes used in immunization, it is an inevitable fact that antibodies with high crossreactivities with such as $N^1$-AcSpm and $N^1$-AcSpd are readily produced. In order to prepare antibodies highly specific to DiAcSpm from antibodies with such various specificities and to make them stably and easily purifiable, it is important to prepare monoclonal antibodies.

By the development of the monoclonal antibody of the invention, a high affinity monoclonal antibody is provided, which makes it possible to select a measuring condition that the concentration of DiAcSpm at which the immunoreaction of solid-phased DiAcSpm is inhibited 50% is 1 nM or less. As a result, it becomes possible to quantitatively determine DiAcSpm (which is contained in a trace amount in urine samples where structure analogs are present abundantly) correctly by enzyme immunoassay, avoiding interference by structure analogs.

2. Preparation of Antigen

Since DiAcSpm is an alkylamine of a low molecular weight, immunizing mice with DiAcSpm does not produce DiAcSpm-specific antibodies. Therefore, an immunizing antigen which has a number of DiAcSpm-analogs as side chains is prepared by binding bovine serum albumin (a carrier protein) to $N^1$-AcSpm by acylamide bond.

In the present invention, an immunizing antigen may be prepared based on a known method (Hiramatsu, K. et al., J. Biochem., 124, 231-236 (1998)). First, the carrier protein BSA is reacted with anhydrous acetylmercaptosuccinic acid (hereinafter referred to as "AMS") to thereby prepare AMS-BSA complex as a reaction product. Further, by coupling AcSpm to AMS-BSA by acylamide bond via a divalent crosslinking agent GMBS (N-(4-maleimidobutyryloxy)succinimide), an immunizing antigen AcSpm-GMB-AMS-BSA is prepared. It should be noted that preparation of antigen is not limited to this method.

3. Immunization with the Antigen and Measurement of Antibody Titers

The animal to be immunized may be a mammal such as mouse, rat or rabbit. Dose of the antigen per animal is 100-1,000 μg in total. Generally, adjuvant and antigen solution are mixed together when immunizing animals with antigen. Examples of adjuvants useful in the invention include Freund's complete adjuvant (FCA), Freund's incomplete adjuvant (FIA) and aluminium hydroxide adjuvant. Immunization is carried out mainly by intravenous, subcutaneous, intraperitoneal or intramuscular injection of the antigen. The immunization interval is not particularly limited. Immunization may be carried out at intervals of several days to several weeks, preferably 2 to 3 weeks, 1 to 10 ten times, preferably 2 to 5 times. Once antibody titers have risen to 2 or more in the absorbance level as a result of the immunization, the animals are left for 2-6 months, preferably 4-6 months, more preferably 6 months, until the antibody titers have decreased to 0.05-1, preferably 0.05-0.5, more preferably 0.05, in the absorbance level.

Then, re-immunization is carried out once or a plurality of times at intervals of several weeks. Several days, preferably 3-5 days, after the final immunization, splenic cells are removed. When the antigen was injected subcutaneously into the planta of the animals, regional lymph nodes are removed 7-13 days, preferably 8-10 days, after a single immunization. Blood samples are taken 1-4 weeks, preferably 1-2 weeks, after immunization.

The blood samples taken are not stored at a low temperature but immediately centrifuged to separate sera. The resultant sera are subjected to serial dilution, followed by measurement of antibody titers by a method such as ELISA (enzyme-linked immunosorbent assay), EIA (enzyme immunoassay) or RIA (radioimmuno assay). Then, final immunization is given to those mice which show high antibody titers to DiAcSpm. However, immunization with the antigen and measurement of antigen titers are not limited to those described above.

4. Preparation of Antibodies to DiAcSpm

Hereinbelow, a method of preparation of antibodies to DiAcSpm will be described. However, preparation method is not limited to this method.

(1) Preparation of Antibody-Producing Cells

Antibody-producing cells are prepared from splenic cells, regional lymph nodes or the like of immunized animals. Although it is preferable to isolate antibody-producing cells alone from cell populations, this isolation is not particularly required. In the preparation of antibody-producing cells, it is preferable to remove tissue debris and erythrocytes as much as possible. As a method of erythrocyte removal, a commercial erythrocyte remover may be used. Alternatively, a neutral buffer ammonium chloride and Tris may be prepared and used. The thus prepared antibody-producing cells will become deteriorated when the subsequent procedure does not start immediately. Therefore, the antibody-producing cells should be left stationary on ice when much time is required until the start of the subsequent procedure.

(2) Cell Fusion

Cell fusion is a process of fusing the above-described antibody-producing cells to myeloma cells to thereby prepare hybridoma cells which semi-eternally continue to proliferate while producing antibodies. As the myeloma cell to be fused to the antibody-producing cell, a commonly available cell strain derived from an animal such as mouse may be used. A preferable cell strain to be used in the invention cannot survive in HAT selection medium (containing hypoxanthine, thymidine and aminopterin) and can survive there only after fusion to antibody-producing cells. Examples of myeloma cells include P3X63-Ag.8.U1(P3U1) and P3/NS 1/1-Ag4-1 (NS I).

Cell fusion is carried out by mixing $1 \times 10^6$ to $1 \times 10^7$ cells/ml of splenic cells or lymph node cells with $1 \times 10^5$ to $1 \times 10^6$ cells/ml of myeloma cells in a commercial, classic cell culture medium such as fetal calf serum (FCS)-free DMEM or RPMI-1640 (preferable cell ratio of splenic cells or lymph node cells to myeloma cells is 5:1) in the presence of a cell fusion promoter. As the cell fusion promoter, polyethylene glycol with an average molecular weight of 200-20000 daltons or the like may be used. Alternatively, it is also possible to fuse antibody-producing cells and myeloma cells in a commercial cell fusion device utilizing electric stimulation (e.g., electroporation). After the fusion, the resultant cells are diluted with HAT medium prepared using, for example, 10-20% (preferably 20%) FCS-containing RPMI1640 medium, seeded in 96-well culture plates at $0.5-3 \times 10^3$ cells/well, and cultured in a $CO_2$ incubator.

(3) Establishment of Hybridomas

Hybridomas of interest are selected from the fused cells. Ten to fourteen days after the cell fusion, cells selected in the HAT medium as described above form colonies. The culture supernatant of each well of colony-positive 96-well plates is collected, followed by examination of the absence or presence of antibody titers to DiAcSpm. As a method of confirmation, enzyme-linked immunosorbent assay (ELISA), radioimmuno assay (RIA) or the like may be used. Since antibodies to BSA (the carrier protein) are also included, BSA antibody positive wells which have high antibody titers to BSA can be excluded by measuring antibody titers to BSA. Once antibody-positive wells have been confirmed, cells are transferred into 24-well or 12-well culture plates.

At this point, the medium is replaced with HT medium not containing aminopterin. This is because aminopterin is a substance inhibiting DNA replication in cells, and DNA replication in cells does not occur in the absence of hypoxanthine and thymidine when aminopterin is remaining in cells even after removal of aminopterin in the medium. After culturing for a while, antibody titers in the culture supernatant are confirmed again. Although this second confirmation is not required in particular, it is preferable to confirm twice because hybridomas are unstable and it is highly possible that antibody production disappears in a very short period. What is important here is to examine crossreactivities with other DiAcSpm analogs in the culture supernatant level by ELISA, RIA, etc. because, as described above, hybridomas having high specificity to DiAcSpm are needed.

Cells in finally selected wells are subjected to cloning to obtain single cells. Briefly, for example, cell suspension is diluted appropriately with 10-20% (preferably 20%) FCS-containing RPMI1640 medium and seeded in 96-well culture plates at 0.3-2 cells/well. The smaller the number of cells seeded in each well of 96-well culture plates, the higher the probability that one cell is seeded in one well. Thus, smaller number is more preferable. Seven to ten days after the seeding of cells, culture supernatants of colony-positive wells are collected. Here, it is preferable to confirm that the colonies are single colonies 3-5 days after the seeding of cells. Antibody titers in the collected culture supernatants are examined. Again, those clones having high specificity to DiAcSpm and low crossreactivities with DiAcSpm analogs are selected. Cells in further selected wells are proliferated to some extent to establish hybridomas. If necessary, cloning may be preformed several times.

(4) Preparation of Monoclonal Antibodies

DiAcSpm specific monoclonal antibodies are purified and prepared from the established hybridomas by the method described below. Briefly, a method in which antibodies are prepared from culture supernatants obtained by culturing hybridomas in a medium with a low serum concentration; a method in which antibodies are prepared from culture supernatants obtained by culturing hybridomas in a commercial serum-free medium; a method in which hybridomas are injected into the abdominal cavities of animals and the resultant abdominal dropsies are collected to prepare antibodies; or the like may be used. Culture supernatants are collected after culturing cells at a concentration of $0.1$-$4 \times 10^5$ cells/ml for 1-2 weeks. In the abdominal dropsy formation method, approx. $0.1$-$1 \times 10^7$ hybridoma cells are administered into the abdominal cavity of an allogenic animal to the mammal from which the myeloma cell derived, to thereby expand the hybridoma cells greatly. One to two weeks thereafter, the abdominal dropsy is collected.

With respect to the culture method, a method using culture flasks, a method using spinner flasks, a method using shaker flasks, a method using bioreactors, and the like may be enumerated. Antibodies may be purified by such methods as a method using protein G affinity column, a method using DiAcSpm affinity column, a method using ammonium sulfate salting out and gel filtration chromatography, ion exchange chromatography, or the like. Any of these known methods may be appropriately selected or used in combination.

The cell strain (hybridoma) which produces the monoclonal antibody of the invention is designated "Anti-DiAcSpm hybridoma CN647" and was deposited under Budapest Treaty at International Patent Organism Depositary (IPOD), the National Institute of Advanced Industrial Science and Technology (AIST) (Tsukuba Central 6, 1-1, Higashi 1-chome, Tsukuba City, Ibaraki-Pref. 305-8566 Japan) on Jun. 18, 2004. The accession number is "FERM BP-10420".

(5) Properties of the Monoclonal Antibody

The monoclonal antibody of the invention has the properties as described below in an antigen competitive inhibition assay system, i.e., an immunoreaction system between a solid-phased diacetylspermine and a specific monoclonal antibody to the diacetylspermine, wherein a sample diacetylspermine or sample diacetylspermidine is also present so that the immunoreaction is inhibited:

(i) The monoclonal antibody satisfies a measuring condition that the 50% inhibition activity against the above-described immunoreaction by the DiAcSpm in the sample is at least 1,000 times as much as the 50% inhibition activity against the above-described immunoreaction by the $N^1$-AcSpd in the sample.

Here, a system is contemplated in which DiAcSpm is immobilized and solid-phased in the bottom of a plate, and a monoclonal antibody to DiAcSpm is added thereto to react with the DiAcSpm. When no competitive substance is present in this reaction system, the monoclonal antibody reacts with the solid-phased DiAcSpm. To this reaction system, free DiAcSpm is added as a sample. Then, this free DiAcSpm reacts with the monoclonal antibody in competition with the solid-phased DiAcSpm. When the binding between the solid-phased DiAcSpm and the monoclonal antibody is inhibited 50%, that is, when the binding activity between the monoclonal antibody and the solid-phased DiAcSpm in the presence of competitive DiAcSpm has decreased to 50% of the binding activity between the monoclonal antibody and the solid-phased DiAcSpm in the absence of free, competitive DiAcSpm, the amount or concentration of the free DiAcSpm at this point can be defined as inhibition activity.

The above-described inhibition activities may be measured for free DiAcSpm and free $N^1$-AcSpd, respectively, and those antibodies which satisfy the following measuring condition may be selected as the antibody of the present invention: the inhibitory activity when free DiAcSpm is used is more than 1,000 times larger than the inhibitory activity when $N^1$-AcSpd present abundantly in urine in a free form is used and more than 100,000 times larger than the inhibitory activity when $N^8$-AcSpd present abundantly in urine in a free form is used. This means that the monoclonal antibody of the invention does not cross-reacts with $N^1$-AcSpd, etc. and is specific to DiAcSpm.

(ii) The concentration of DiAcSpm in the sample when the condition described in (i) above is satisfied is 1 nM or less, preferably 0.1-2 nM.

The antibody of the invention having the above-described properties has affinity at least 1,000 times as much as the affinity of the monoclonal antibody disclosed in Japanese Unexamined Patent Publication No. H11-75839. It should also be noted that the immunizing method used in the invention for obtaining the above-described antibody is a method in which high affinity antibody-producing B cells are retained in memory in the living body, and these memory B cells are activated efficiently. This means that the antibody of the invention has high affinity for DiAcSpm.

5. Method of Tumor Detection

Since DiAcSpm can be used as a clinical marker for cancer (tumor marker), it is possible to detect a tumor by reacting the antibody of the invention with a biological sample to thereby measure DiAcSpm in the biological sample and using the measurement result as an indicator. The measurement of DiAcSpm may be performed by any of the conventional hapten immunoassays and is not particularly limited. The tumor to be detected is not particularly limited. For example, at least one selected from large bowel cancer, urinary tract malignant tumors (e.g., prostate cancer, kidney cancer, bladder cancer and testis tumor), breast cancer, pancreatic cancer and biliary tract cancer may be given. The cancer to be detected may be one or a complication of two or more cancers.

Biological samples are taken from patients suspicious of cancer or subjects of health examination, followed by preparation of samples for DiAcSpm measurement. Examples of biological samples include blood, urine and tissue. Urine is preferable because it is easy to handle and imposes less burden on patients. From the viewpoint of early diagnosis of cancer, blood is preferable though DiAcSpm is contained only in a trace amount.

Subsequently, the thus prepared sample for DiAcSpm measurement is reacted with the above-described antibody. Measurement of DiAcSpm may be performed by conventional ELISA. First, microplates are coated with the antigen (DiAcSpm) in advance of performing the measurement by ELISA. On the other hand, DiAcSpm in the biological sample and DiAcSpm in the standard solution are pre-reacted with the anti-DiAcSpm specific antibody, and the resultant reaction solutions are plated on the microplates. The antibody remaining unreacted binds to the DiAcSpm on the microplate. Then, HRP-labeled anti-rabbit IgG antibody (which is a secondary antibody) is added to the microplate for reaction. Finally, the DiAcSpm contained in the biological sample is quantitatively determined by the color development reaction catalyzed by HRP. The labeling enzyme used in the secondary antibody is not limited to HRP (peroxidase); alkaline phosphatase, malate dehydrogenase, α-glucosidase, α-galactosidase, or the like may also be used.

6. Method of Evaluation of Tumors

In the present invention, the state of tumor can be evaluated using, as an indicator, the detection results obtained by the detection method described in above subsection 5. Detection results exceeding the specific standard value are classified as DiAcSpm positive, and detection results below the specific standard value are classified as DiAcSpm negative. When the result is positive, it is judged that the relevant patient or subject may have cancer, and then the state of the tumor can be evaluated.

The state of tumor means the presence or absence of tumor or the progression thereof. Specifically, the presence or absence of cancer occurrence, the progression of cancer, the degree of the malignancy of cancer, the presence or absence of cancer metastasis, the presence or absence of cancer recurrence, and the like may be enumerated. In the above-described evaluation, one state may be selected. Alternatively, a plurality of states may be selected in an appropriate combination. In order to evaluate the presence or absence of cancer, whether the relevant patient has developed cancer or not is judged. The degree of the malignancy of cancer can be an indicator showing how much advanced the cancer is. This degree may be evaluated by staging the cancer or classifying the cancer into the so-called early cancer or advanced cancer. Cancer metastasis is evaluated by whether or not neoplasms are occurring at distant sites from the primary lesion. Recurrence is judged by whether or not the cancer appeared again after intermission or remission.

7. Kit Comprising the Antibody of the Invention

In the present invention, it is possible to use the monoclonal antibody to DiAcSpm in a DiAcSpm detection kit or as a reagent for DiAcSpm detection.

Conventionally, when polyamines are measured in general biochemical tests, urinary polyamines were measured collectively as similar structures. Relations between respective similar structures and disease conditions have hardly been examined (Shunichiro Kubota, NIPPON-RINSHO (Japan Clinical Medicine) 53, Special Issue, pp. 501-505 (1995)). Then, a method has been established in which amounts of urinary polyamines are measured discretely and it has been confirmed that especially DiAcSpm (one species of polyamine) is highly elevated at the time of occurrence and at the time of recurrence after treatment of prostate cancer or large bowel cancer. This means that that, if it is possible to develop a method of measuring diacetylpolyamines easily and accurately, there would be a large demand for diacetylpolyamines as novel tumor makers in clinical cancer diagnosis. Further, since the antibody of the invention is capable of detecting a trace amount of DiAcSpm with high sensitivity, application of the antibody to measurement of DiAcSpm in blood (which has been impossible so far) or to detection of abnormality at an early stage can be expected.

The present inventors have contemplated as a DiAcSpm detection system an AcSpm measuring system by competitive ELISA using the DiAcSpm monoclonal antibody. As a solid-phased antigen, monoacetylspermine coupled to a peptide by acylamide bond and having a DiAcSpm-mimicking structure (AcSpm-HMC-peptide) may be used. This antigen is obtained by coupling monoacetylspermine to a water-soluble polypeptide by acylamide bond via bivalent crosslinking reagent (HMCS; N-(8-Maleimidocapryloxy) succinimide) (Hiramatsu, K. et al., J. Biochem., 124, 231-236 (1998)).

The kit of the present invention must be capable of measuring DiAcSpm with high sensitivity. Further, this kit is required to have reproducibility if it is intended to be used in clinical scenes of cancer diagnosis. Upon such a premise, the present invention aimed at establishment of a measuring system for DiAcSpm as a tumor diagnostic agent.

The tumor diagnostic agent of the invention is capable of setting its standard region ranging from 0.1 to 2 nM by adjusting the solid-phased antigen concentration toward the low concentration side. The solid-phased antigen concentration is 0.1-1 µg/ml, preferably 0.07 µg/ml. As a result, sensitivity and measuring accuracy sufficient to measure urinary DiAcSpm can be achieved.

Measurement accuracy is an indicator which shows to what extent individual measured values would vary when one assay has been performed using one same sample aliquoted into a plurality of test tubes or wells. Statistically, measurement accuracy is expressed as coefficient of variation (CV), that is, ratio (%) of standard deviation to mean. In the present invention, this CV is referred to as reproducibility. Reproducibility is 15% or less, preferably 10% or less, more preferably 5% or less.

The kit of the present invention has the following performances: actually measured minimum detection value: (0.1 nM); detection sensitivity in sample measurement: 0.4 nM (0.1×4). Within-day reproducibility is 10% or less, preferably around 5%. Between-day reproducibility is 10% or less, preferably about 8-10%. In both reproducibilities, CV is 10% or less. With respect to the influence of co-existing substances, conjugated bilirubin, glucose, hemoglobin and ascorbic acid do not give any influence upon DiAcSpm measurement.

When the monoclonal antibody of the invention is used as a diagnostic agent, the monoclonal antibody may be mixed with solvents or solutes and prepared into the form of a composition. For example, the monoclonal antibody may be combined with distilled water, pH-buffering reagents, salts, proteins, surfactants, and so forth.

The diagnostic agent may also contain antigen-immobilized microplates, DiAcSpm standard product (STD), antibody dilutions, HRP-labeled anti-rabbit IgG antibody, OPD (ortho-phenylene-diamine) tablets, substrate solution, reaction termination solution, concentrated washing solution or the like selected appropriately, in addition to the antibody of the invention. As the labeling enzyme, alkaline phosphatase, malate dehydrogenase, α-glucosidase, α-galactosidase, or the like may also be used other than HRP (peroxidase).

As reaction media, buffers which give optimum conditions for reaction or are useful in stabilizing reaction products, stabilizers for reactants, and the like are also included in the kit.

Hereinbelow, the present invention will be described in more detail with reference to the following Experimental Examples and Examples. However, the present invention is not limited to these Experimental Examples and Examples.

EXAMPLE 1

Preparation of Diacetylspermine (DiAcSpm) Specific Monoclonal Antibodies (1) Preparation of Antigen The immunizing antigen was prepared as described below, based on the known method (Hiramatsu, K. et al., J. Biochem., 124, 231-236 (1998)). Since DiAcSpm is an alkylamine of a low molecular weight, it is impossible to obtain DiAcSpm-specific antibodies by immunizing rabbits with DiAcSpm itself. Therefore, immunizing antigen AcSpm-GMB-AMS-BSA which has a number of DiAcSpm-mimicking structures as side chains was prepared by coupling bovine serum albumin (hereinafter abbreviated to "BSA") (a carrier protein) to $N^1$-AcSpm by acylamide bond. Briefly, BSA which functions as a carrier protein was reacted with AMS, and the reaction product was purified with a Sephadex G-25 gel filtration column to thereby prepared AMS-BSA. On the other hand, AcSpm was coupled to AMS-BSA by acylamide bond via a bivalent crosslinking reagent GMBS to thereby obtain GMB-AcSpm. Further, AMS-BSA was reacted with GMB-AcSpm to thereby obtain the immunizing antigen AcSpm-GMB-AMS-BSA.

(2) Evaluation of the Antigen

The antigen was evaluated using DiAcSpm specific polyclonal antibody. Six lots of the antigen prepared in (1) above were examined on their activities to inhibit the reaction of anti-DiAcSpm polyclonal antibody with solid-phased AcSpm-HMC-AcSpm, by the method described later in Experimental Example 1.

The results revealed that lots No. 1 and No. 6 have the highest inhibition activity and lot No. 5 comes next (FIG. 1). Therefore, these lots are relatively optimal antigen as a structure analog of DiAcSpm. They were selected as the immunizing antigen. Since the quantities of these lots were limited, the antigen used for one animal was not necessarily the same lot.

(3) Immunization of Mice

Figure 2:
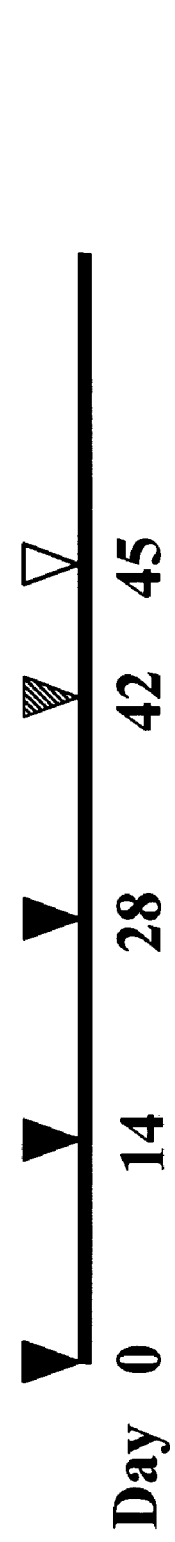
FIG. 2 is a diagram showing an outline of immunization schedules and methods.
Figure 2:
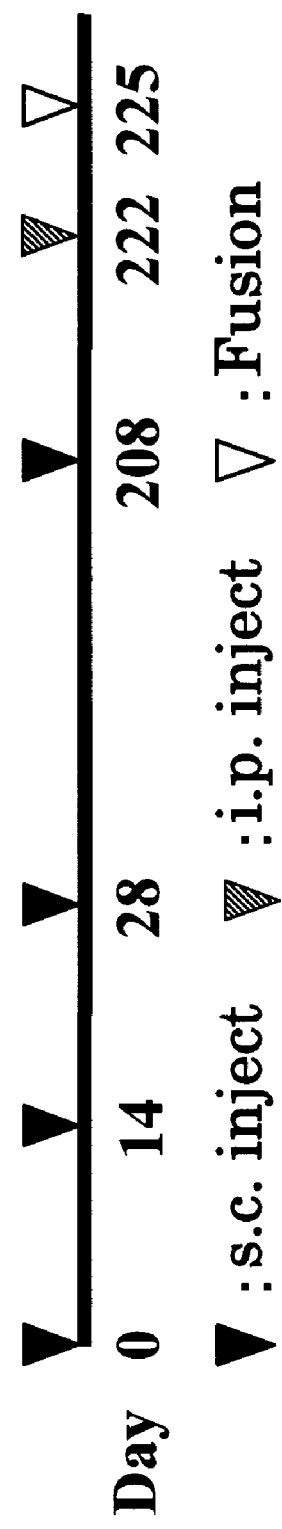

Mice were immunized using the three lots of antigen selected in (2) above. Immunization was performed by two methods. An outline of the immunizing methods is shown in FIG. 2. The first method was performed as described below. Briefly, the immunizing antigen prepared to give a concentration of 2 mg/ml was mixed with an equal volume of FCA to form an emulsion, which was administered subcutaneously in the back of mice (100 µl/mouse). Subsequently, an emulsion prepared by mixing equal volumes of 1 mg/ml immunizing antigen and FIA was administered subcutaneously in the back of mice at intervals of two weeks (100 µl/mouse). The antigen was administered 3 times in the total, followed by examination of antibody titers by ELISA. To those mice which showed high antibody titers, an emulsion prepared from 1 mg/ml immunizing antigen and IFA was administered into the abdominal cavity (100 µl/mouse) as a final immunization. Three days after the final immunization, the spleen was removed for cell fusion. The second method was performed as described below. Briefly, the same procedures as in the first method were performed up to the third administration of the immunizing antigen. Then, mice were left for 6 months until the antibody titers decreased, and the emulsion prepared from 1 mg/ml immunizing antigen and IFA was re-administered subcutaneously in the back of mice. Two weeks thereafter, the emulsion prepared from 1 mg/ml immunizing antigen and IFA was administered into the abdominal cavity of mice as a final immunization. Three days after the final immunization, the spleen was removed for cell fusion.

(4) Preparation of Splenic Cells and Cell Fusion

The removed spleen was ground to prepare splenic cells containing anti-DiAcSpm antibody producing cells. In both of the immunization methods, splenic cells could be prepared at approx. $1 \times 10^8$ cells/mouse. On the other hand, myeloma cell P3U1 was cultured. On the day of cell fusion, the viable cell ratio of P3U1 was 95% or more. The splenic cells and P3U1 cells were mixed at 5:1 and fused using polyethylene glycol with a molecular weight of 1,450 at a concentration of 50% concentration. After the fusion, the resultant cells were washed with medium, suspended in HAT medium, and seeded in 96-well culture plates so that $0.5 \times 10^5$ splenic cells are placed in each well. Ten to twelve days after the cell fusion, colonies were examined in each well. As a result, colony positive ratio was 95% or more in both immunization methods 1 and 2.

(5) Screening for Antibody Production Positive Clones

On day 12 after the cell fusion, culture supernatants were recovered and screened for antibody production positive clones by the method described later in Experimental Example 2. In immunization method 1, 24 wells out of 1,320 were BSA negative and DiAcSpm positive. In immunization method 2, 247 wells out of 2,880 were BSA negative and DiAcSpm positive. Cells of these selected wells were transferred into 24-well plates, cultured for 1-2 days, and screened again by the method described in Experimental Example 2. Finally, 16 wells were found DiAcSpm positive in immunization method 1, and 208 wells were found DiAcSpm positive in immunization method 2.

(6) Crossreactivity Test on Antibody Production Positive Clones

Out the DiAcSpm positive clones obtained above, 51 clones with relatively high antibody titers were selected and tested for crossreactivity with $N^1$-AcSpd (which is present in urine abundantly and believed to cross-react relatively easy from the results of researches made so far) by the method described later in Experimental Example 3. As a result, with respect to two wells, the 50% reaction inhibition activity of $N^1$-AcSpd was about 800 times as much as that of DiAcSpm; with respect to one well, the 50% reaction inhibition activity of $N^1$-AcSpd was 3,000 times as much as that of DiAcSpm; and with respect to the other wells, the 50% reaction inhibition activity of $N^1$-AcSpd was 0-200 times as much as that of DiAcSpm.

(7) Cloning

Figure 3:
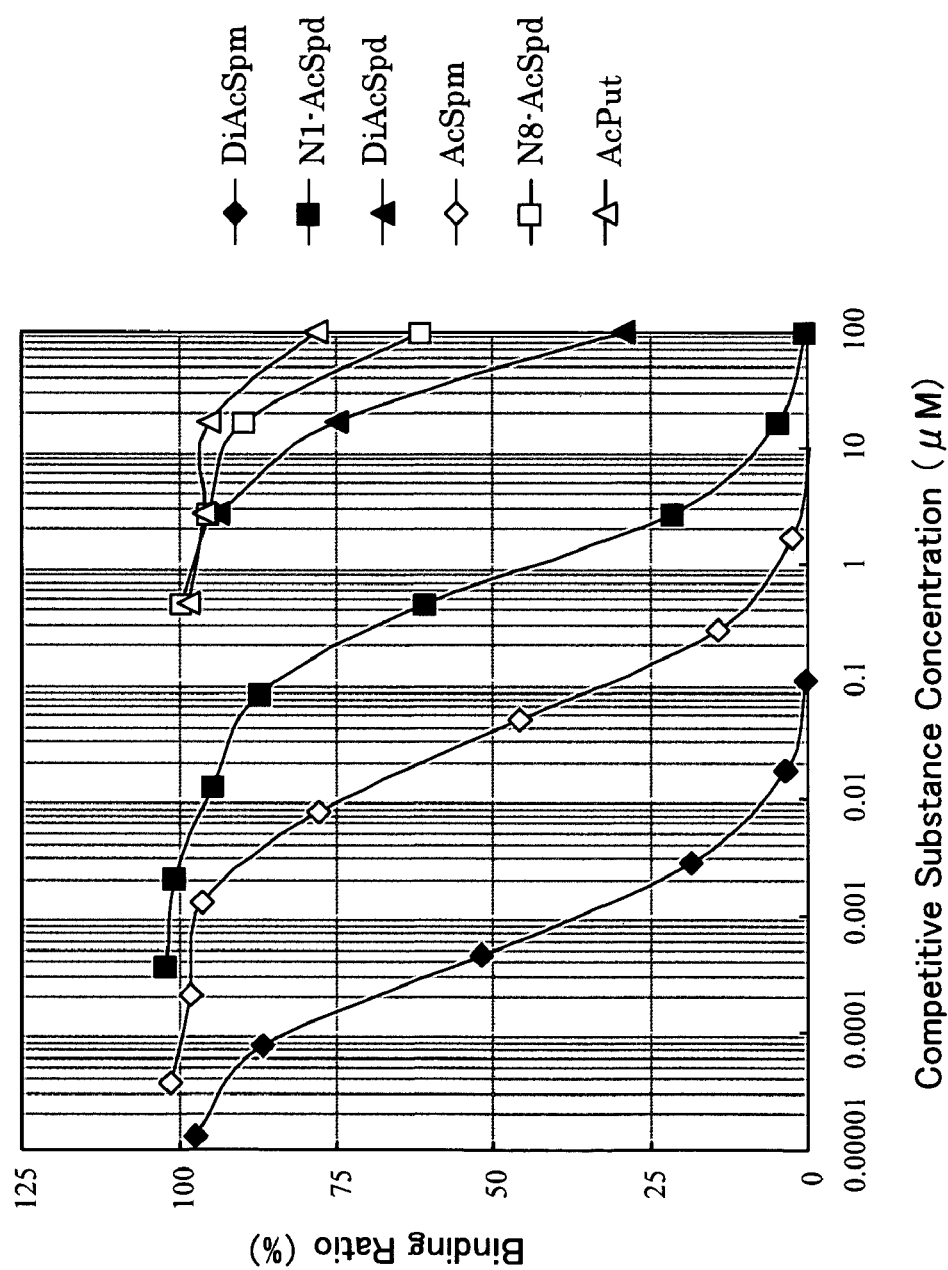
FIG. 3 is a graph showing binding inhibition activities of various substances in culture supernatant of CN647 strain.

Cells of the one well which showed high specificity to DiAcSpm were cloned by the limiting dilution culture method. Briefly, cells were diluted with 20% FCS-containing RPMI medium to a density of 2.5 cells/ml and added to two 96-well culture plates at 200 µl/well. After five days, single colonies were examined. As a result, a single colony was confirmed in 17 wells out of the two 96-well plates. After 10 days, antibody titers to DiAcSpm were measured in culture supernatants by the method described in Experimental Example 2. Three wells were positive. Cells in these three wells were cultured further and tested for crossreactivities with AcSpm, $N^1$-AcSpd, $N^8$-AcSpd, DiAcSpd and AcPut by the method described in Experimental Example 3. The results revealed that with respect to all of the three wells, the 50% inhibition activity of DiAcSpm was about 1,000 times as much as that of $N^1$-AcSpd, about 70 times as much as that of AcSpm, about 100,000 times as much as that of DiAcSpm, and more than about 500,000 times larger than that of $N^8$-AcSpd and that of AcPut. Thus, antibodies sufficient to achieve the object have been obtained (FIG. 3). One of them was designated "established clone CN647".

(8) Purification of Antibody

A monoclonal antibody of interest was purified from established clone CN647 as described below. First, established clone CN647 was suspended in a commercial serum-free medium (Hybridoma SFM; Invitrogen) to give a density of $4 \times 10^5$ cells/ml. A 50 ml aliquot of the cell suspension was placed in a T225 flask and cultured at 37° C. under 5.0% $CO_2$ for about two weeks. Then, the culture supernatant was recovered, applied to a protein G column, and eluted with glycine buffer (pH 3) to thereby purify a monoclonal antibody. The thus purified antibody retained the activity. Further, typing of the purified antibody revealed that this antibody is IgG1κ. This monoclonal antibody was used in a DiAcSpm measuring kit.

EXAMPLE 2

Measurement of DiAcSpm Using the Kit

(1) Establishment of the Conditions of the Kit

Figure 4:
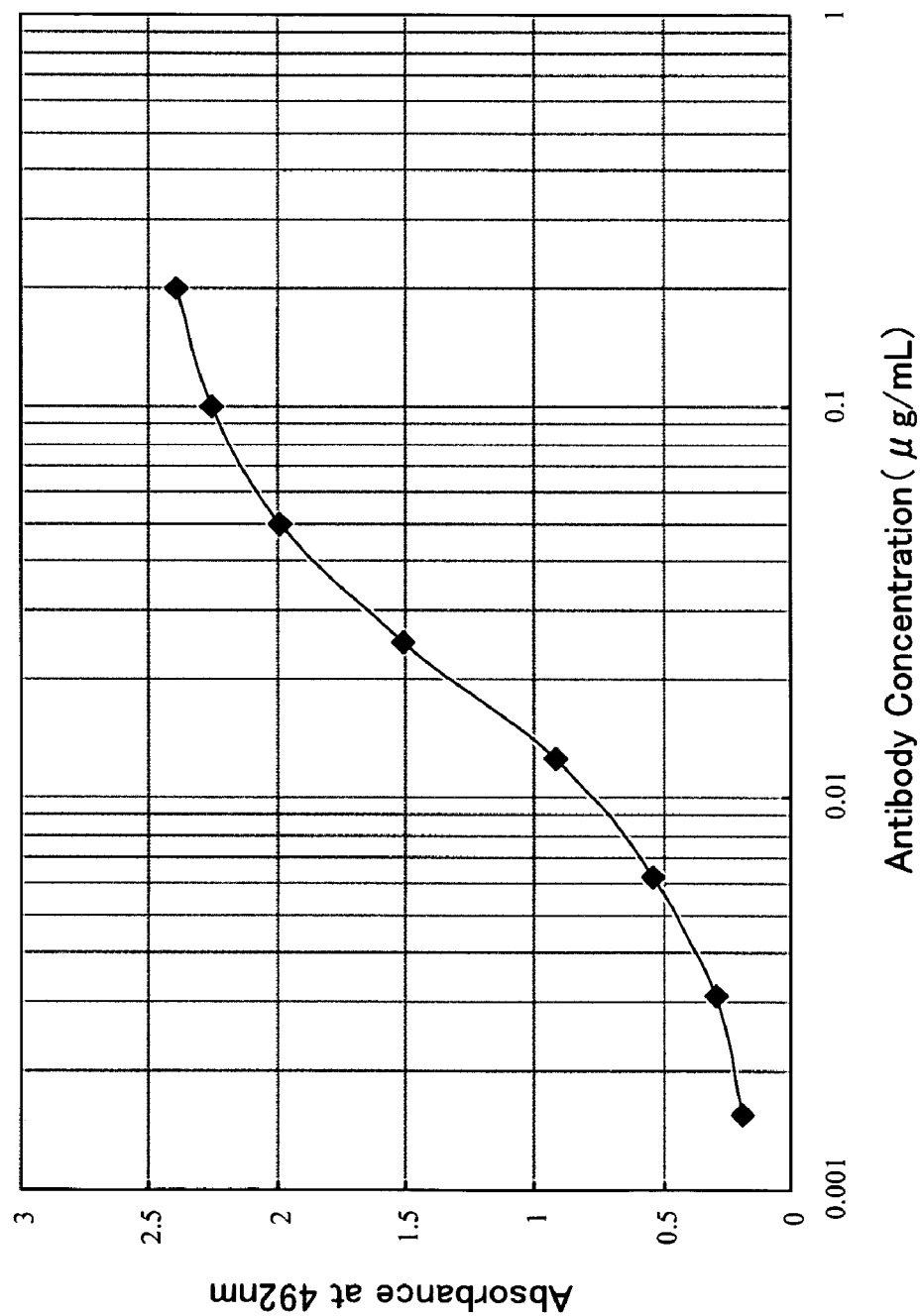
FIG. 4 is a graph showing examination of the concentration of anti-DiAcSpm monoclonal antibody using a tumor diagnostic agent.

As a measuring kit, competitive ELISA using a solid-phased antigen AcSpm-HMC-peptide was performed based on known methods (Hiramatsu, K. et al., J. Biochem., 124, 231-236 (1998)). As the primary antibody, the monoclonal antibody prepared in Example 1 was used. As the secondary antibody, a commercial, goat-derived HRP-labeled anti-mouse IgG antibody (KPL) was used. The concentration of the solid-phased antigen was set at 0.07 μg/ml based on the concentration employed in a kit using anti-DiAcSpm polyclonal antibody. With respect to the concentration of anti-DiAcSpm monoclonal antibody to be used, 15 ng/ml was selected so that 40% of the maximum reaction efficiency (the point at which the absorbance at 492 nm becomes 1) is achieved when the concentration of the solid-phased antigen AcSpm-HMC-peptide is 0.07 μg/ml (FIG. 4). The dilution ratio of the goat-derived HRP-labeled anti-mouse IgG antibody was set at 2,500-fold from experience.

Further, in order to evaluate the accuracy and performance of DiAcSpm measurement ELISA, within-day reproducibility (N=18) and between-day reproducibility (N=7) were obtained using two different control samples (called Sample A and Sample B) and evaluated. As a result, the within-day reproducibility was CV=6.34% on Sample A and CV=9.278% on Sample B; and the between-day reproducibility was CV=11.605 on Sample S1 and CV=12.835 on Sample S2 (Table 1). Therefore, it was found that the kit is reliable in both reproducibilities.

TABLE 1

Within-Day Reproducibility and Between-Day Reproducibility

| | Within-day reproducibility | | | Between-day reproducibility | |
|---|---|---|---|---|---|
| sample No. | A | B | | S1 | S2 |
| 1 | 1.298 | 0.417 | 1 | 1.310 | 0.491 |
| 2 | 1.191 | 0.473 | 2 | 1.580 | 0.443 |
| 3 | 1.238 | 0.493 | 3 | 1.338 | 0.348 |
| 4 | 1.364 | 0.424 | 4 | 1.215 | 0.387 |
| 5 | 1.292 | 0.538 | 5 | 1.335 | 0.411 |
| 6 | 1.429 | 0.535 | 6 | 1.614 | 0.349 |
| 7 | 1.259 | 0.540 | 7 | 1.6044 | 0.4401 |
| 8 | 1.217 | 0.537 | mean | 1.428 | 0.410 |
| 9 | 1.248 | 0.519 | SD | 0.165736952 | 0.052668672 |
| 10 | 1.270 | 0.533 | CV(%) | 11.60491728 | 12.85295914 |
| 11 | 1.298 | 0.523 | | | |
| 12 | 1.358 | 0.432 | | | |
| 13 | 1.276 | 0.500 | | | |
| 14 | 1.553 | 0.487 | | | |
| 15 | 1.345 | 0.540 | | | |
| 16 | 1.316 | 0.454 | | | |
| 17 | 1.321 | 0.472 | | | |
| 18 | 1.316 | 0.420 | | | |
| mean | 1.310 | 0.491 | | | |
| SD | 0.083 | 0.046 | | | |
| CV(%) | 6.343 | 9.278 | | | |

(2) Basic Data of the Kit

First, under the conditions established in (1) above, crossreactivities of structure analogs of DiAcSpm with DiAcSpm in urine samples were examined. Briefly, the 50% inhibition activity concentrations of DiAcSpm, $N^1$-AcSpm, DiAcSpd, $N^1$-AcSpd, $N^8$-AcSpd and DiAcPut in the kit were examined, and the crossreactivities of other structure analogs with DiAcSpm in urine were calculated. As a result, crossreactivity with $N^1$-AcSpd (whose crossreactivity is most apprehended) was 1.62%; crossreactivity with AcSpm was 0.54%; crossreactivity with DiAcSpd was 0.002%; crossreactivity with $N^8$-AcSpd was 0.01%; crossreactivity with AcPut was 0.01%; and the total crossreactivity was 2.17% (Table 2).

TABLE 2

Crossreactivities of Urinary Structure Analogs of DiAcSpm with DiAcSpm

| | DiAcSpm | AcSpm | DiAcSpd | N1-AcSpd | N8-AcSpd | AcPut | Total |
|---|---|---|---|---|---|---|---|
| $Ki_{DiAcSpm}/Ki_{"S"}$ (%) ... (1) | 100 | 1.7072 | 0.0008 | 0.0610 | 0.0003 | 0.0001 | |
| Urinary ratio to DiAcSpm ... (2) | 1.00 | 0.314 | 2.95 | 26.5 | 23.7 | 93.8 | |
| Crossreactivity (1) × (2) (%) | 100 | 0.54 | 0.002 | 1.62 | 0.01 | 0.01 | 2.17 |

Figure 5:
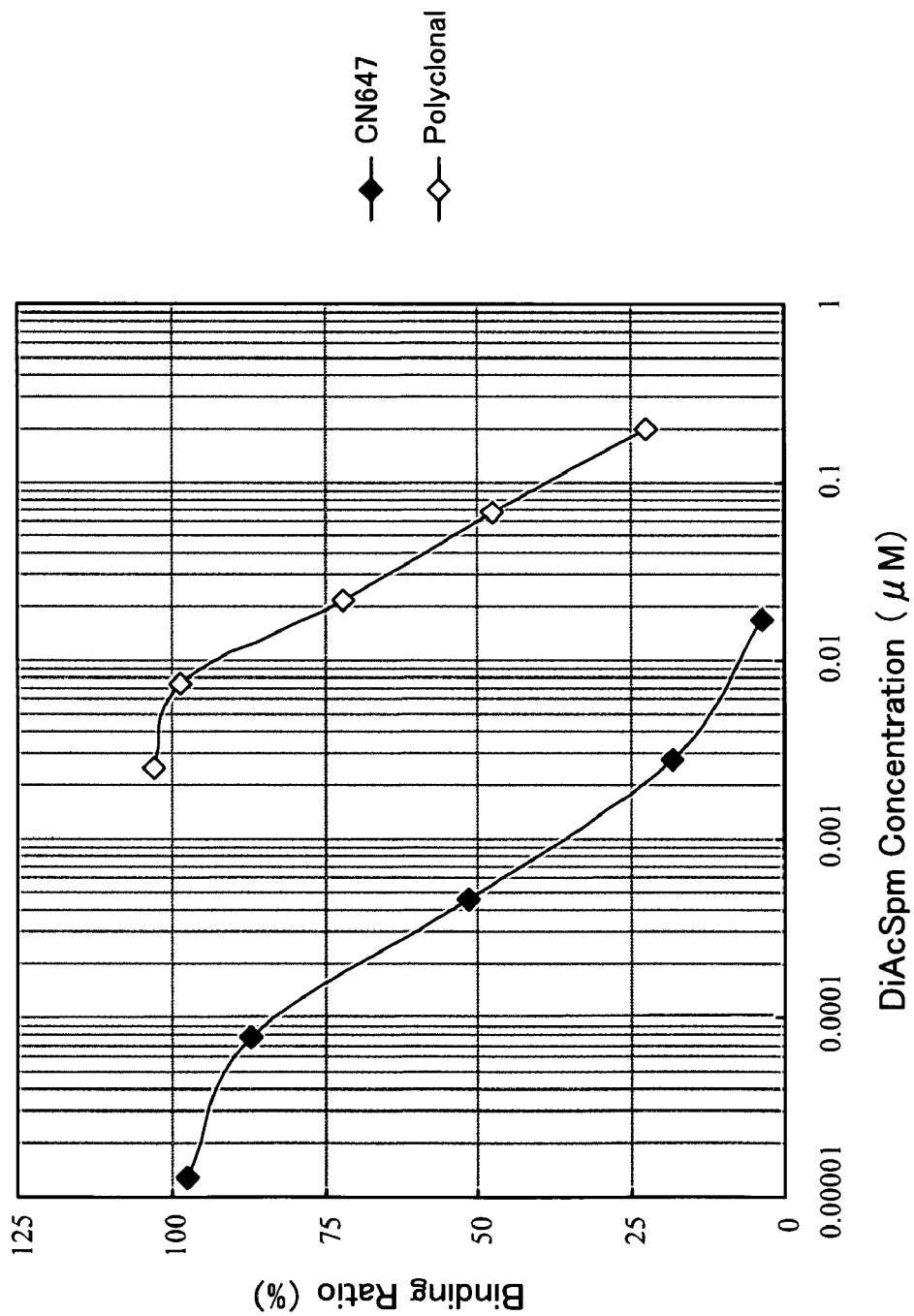
FIG. 5 is a graph showing comparison between CN647 and anti-DiAcSpm polyclonal antibody.

Further, the anti-DiAcSpm monoclonal antibody of the invention was compared with an existing anti-DiAcSpm polyclonal antibody (Transgenic) on reactivity with DiAcSpm. The results revealed that the sensitivity of the monoclonal antibody of the invention is about 100 times as much as that of the anti-DiAcSpm polyclonal antibody (FIG. 5). Therefore, it is expected that the monoclonal antibody of the invention is capable of measuring DiAcSpm in a still wider range of biological samples.

Subsequently, addition/recovery test was performed.

Figure 6:
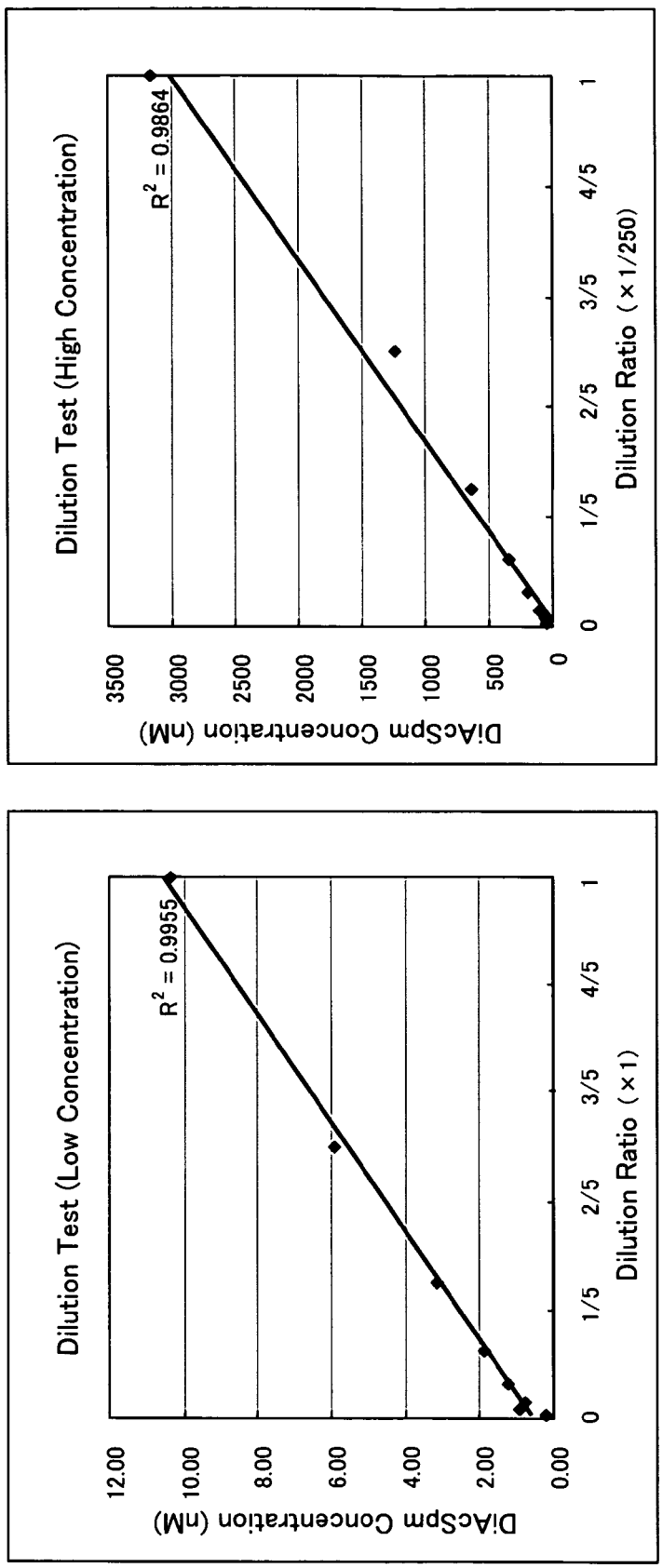
FIG. 6 is graphs showing the results of dilution tests using two urine samples with different DiAcSpm concentrations.

In the case of the polyclonal antibody kit, 4-fold or more dilution of urine samples yield good measuring results. Therefore, it was judged that the kit of the present invention having still higher sensitivity will work sufficiently without performing addition/recovery test. Further, dilution test was performed on two urine samples with different DiAcSpm concentrations. A good dilution curve was obtained from both samples (FIG. 6).

Figure 7:
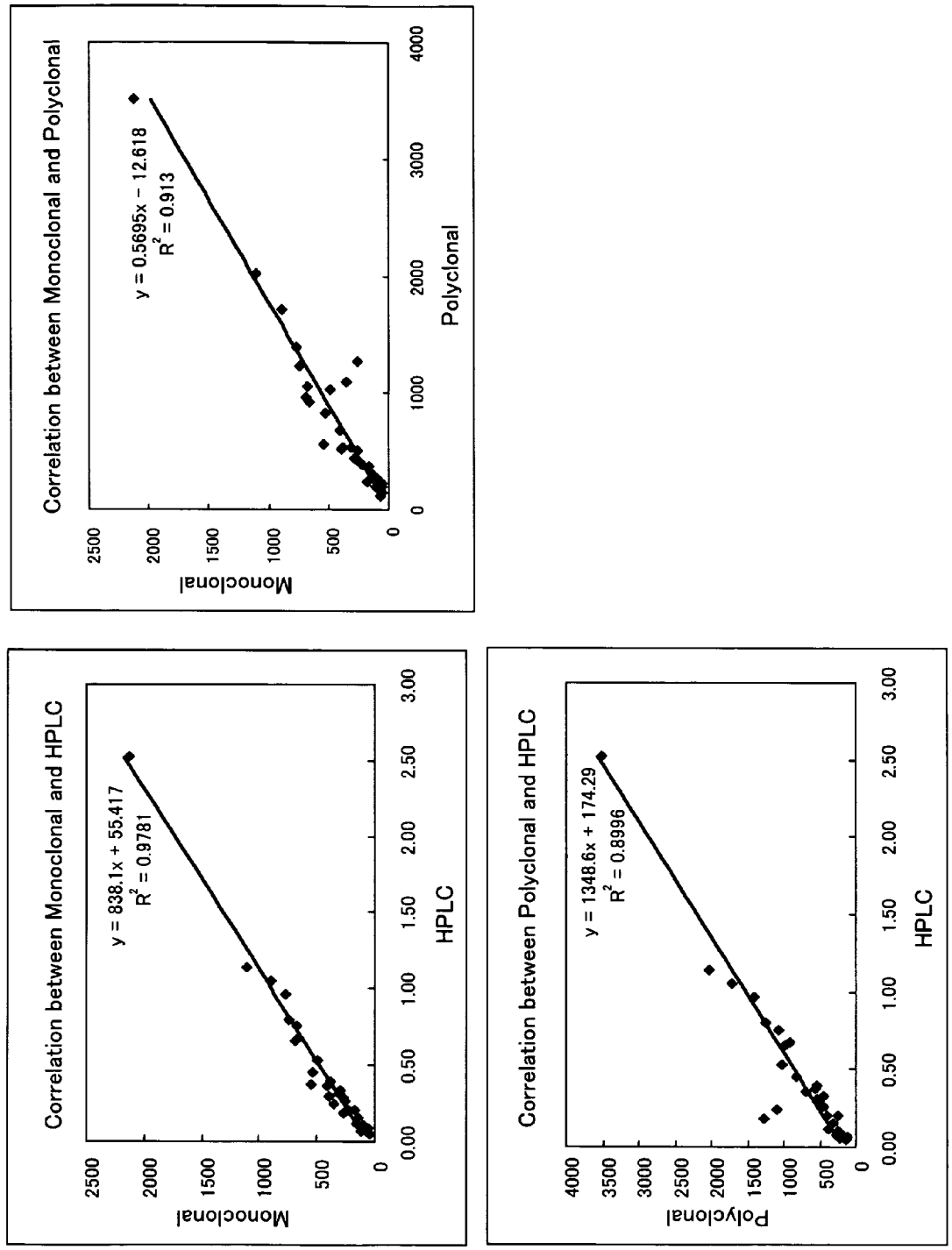
FIG. 7 is graphs showing correlations between competitive ELISA and HPLC using the antibody of the invention.

Subsequently, in order to evaluate the ELISA kit for measuring DiAcSpm further, urine samples measured by HPLC which serve as reference were measured by the ELISA kit of the invention, and correlation with HPLC was examined. As a result, correlation with HPLC was $R^2=0.9781$ which is a very good result (FIG. 7). From these results, it was demonstrated that the ELISA kit of the invention is capable of measuring urinary DiAcSpm with high accuracy.

Experimental Example 1

Method of Evaluation of Antigen

AcSpm-HMC-peptide diluted with PBS (pH 7.0) to 0.07 μg/ml was added to 96-well microtiter plates at 50 μl/well as an antigen to be solid-phased, and left at 25° C. for 1.5 hours. Subsequently, the plates were washed with 0.05% Tween20-containing PBS (pH 7.0) (PBST) three times. Then, 0.5% gelatin-containing PBST (blocking solution) was added thereto at 200 μl/well and left at 25° C. for 1 hour. The plates were frozen at −30° C. overnight to freeze the blocking solution for freeze-drying to thereby prepare freeze-dried plates. To each well of dilution plates, 70 μl of 10 μg/ml anti-DiAcSpm polyclonal antibody and 70 μl of each lot of the immunizing antigen AcSpm-GMB-AMS-BSA with serially varied concentration were mixed and added, and left at 25° C. for 1 hour for pre-reaction. Subsequently, to each well of the freeze-dried plates prepared in Experimental Example 1, 300 μl of PBST was added, left at 25° C. for 30 minutes and then re-washed with PBST once. To each well of these plates, 50 μl of the pre-reacted reaction solution was added and left at 25° C. for 1 hour. Then, after washing with PBST three times, 50 μl of 80-fold dilution of HRP-labeled anti-rabbit IgG antibody (Bio-Rad) was added to each well and left at 25° C. for 1 hour. Subsequently, after washing with PBST three times, 100 μl of o-phenylenediamine solution diluted with 0.012% hydrogen peroxide-containing 0.1 M citrate phosphate buffer (pH 5.0) to 0.5 mg/ml was added to each well and left at 25° C. for 9 minutes. Then, absorbances at 492 nm were measured with an ELISA reader.

Experimental Example 2

Antibody Screening Method

Freeze-dried plates prepared in the same manner as in Experimental Example 1, and BSA immobilized plates prepared by adding 50 μl of BSA diluted with PBS (pH 7.0) to 1 mg/ml to each well of 96-well microtiter plates and leaving at 25° C. overnight were used in the following procedures. To each well of the freeze-dried plates and the BSA immobilized plates, 300 μl of PBST was added, left at 25° C. for 30 minutes, and re-washed with PBST once. After washing, 50 μl of non-diluted culture supernatant was added to each well and left at 25° C. for 40 minutes. Then, after washing with PBST three times, 50 μl of 80-fold dilution of HRP-labeled anti-mouse IgG antibody (KPL) was added to each well and left at 25° C. for 40 minutes. Subsequently, after washing with PBST three times, 100 μl of o-phenylenediamine solution diluted with 0.012% hydrogen peroxide-containing 0.1 M citrate phosphate buffer (pH 5.0) to 0.5 mg/ml was added to each well and left at 25° C. for 9 minutes. Then, absorbances at 492 nm were measured with an ELISA reader.

Experimental Example 3

Crossreactivity Test

Antibody titers in diluted culture supernatants were measured by the method described in Experimental Example 2. Based on the results, the dilution rate with which the absorbance at 492 nm becomes 1 was selected. To each well of dilution plates, 70 μl of culture supernatant diluted at the dilution rate selected above and 70 μl of DiAcSpm solution with serially varied concentration or a structure analog of DiAcSpm ($N^1$-AcSpm, $N^1$-AcSpd, DiAcSpd, or the like) with serially varied concentration were mixed and added, and then left at 25° C. for 1 hour for pre-reaction. Subsequently, to each well of freeze-dried plates prepared in the same manner as in Experimental Example 1, 300 μl of BST was added, left at 25° C. for 30 minutes and re-washed with BST once. To the resultant plates, the pre-reacted reaction solution was added at 50 μl/well and left at 25° C. for 1 hour. Then, after washing with PBST three times, 50 μl of 80-fold dilution of HRP-labeled anti-mouse IgG antibody (KPL) was added to each well and left at 25° C. for 1 hour. Subsequently, after washing with PBST three times, 100 μl of o-phenylenediamine solution diluted with 0.012% hydrogen peroxide-containing 0.1 M citrate phosphate buffer (pH 5.0) to 0.5 mg/ml was added to each well and left at 25° C. for 9 minutes. Then, absorbances at 492 nm were measured with an ELISA reader.

What is claimed is:

1. An anti-diacetylspermine specific monoclonal antibody which is produced by a cell strain having an accession number of FERM BP-10420.

2. An anti-diacetylspermine specific monoclonal antibody-producing cell strain having an accession number of FERM BP-10420.

3. A reagent for detecting diacetylspermine, comprising an anti-diacetylspermine specific monoclonal antibody which is produced by a cell strain having an accession number of FERM BP-10420.

* * * * *